United States Patent
Pazenok et al.

(10) Patent No.: US 9,145,370 B2
(45) Date of Patent: Sep. 29, 2015

(54) PROCEDURE FOR THE DECARBOXYLATION OF 3,5-BIS(HALOALKYL)-PYRAZOLE-4-CARBOXYLIC ACID DERIVATIVES

(71) Applicants: BAYER CROPSCIENCE AG, Monheim (DE); CENTRE NATIONAL DE LA RECHERCHE SCIENTIFIQUE (CNRS), Paris Cedex (FR)

(72) Inventors: Sergii Pazenok, Solingen (DE); Jean-Pierre Vors, Saint Foy Les Lyon (FR); Frederic R. Leroux, Herrlisheim (FR); Florence Giornal, Caderousse (FR)

(73) Assignees: BAYER CROPSCIENCE AG, Monheim (DE); CENTRE NATIONAL DE LA RECHERCHE SCIENTIFIQUE (CNRS), Paris Cedex (FR)

( * ) Notice: Subject to any disclaimer, the term of this patent is extended or adjusted under 35 U.S.C. 154(b) by 0 days.

(21) Appl. No.: 14/422,891

(22) PCT Filed: Aug. 28, 2013

(86) PCT No.: PCT/EP2013/067809
§ 371 (c)(1),
(2) Date: Feb. 20, 2015

(87) PCT Pub. No.: WO2014/033164
PCT Pub. Date: Mar. 6, 2014

(65) Prior Publication Data
US 2015/0225350 A1 Aug. 13, 2015

(30) Foreign Application Priority Data
Aug. 30, 2012 (EP) .................... 12356019

(51) Int. Cl.
*C07D 231/12* (2006.01)
*C07D 231/14* (2006.01)

(52) U.S. Cl.
CPC ............ *C07D 231/14* (2013.01); *C07D 231/12* (2013.01)

(58) Field of Classification Search
None
See application file for complete search history.

(56) References Cited

U.S. PATENT DOCUMENTS

| 7,943,774 B2 | 5/2011 | Cristau et al. |
| 8,524,743 B2 | 9/2013 | Cristau et al. |
| 8,569,509 B2 | 10/2013 | Cristau et al. |
| 8,669,277 B2 | 3/2014 | Oberholzer et al. |
| 2011/0046178 A1 | 2/2011 | Cristau et al. |
| 2011/0124501 A1 | 5/2011 | Cristau et al. |
| 2013/0090476 A1 | 4/2013 | Cristau et al. |
| 2013/0090477 A1 | 4/2013 | Cristau et al. |
| 2014/0031553 A1 | 1/2014 | Cristau et al. |
| 2014/0057945 A1 | 2/2014 | Cristau et al. |
| 2014/0127322 A1 | 5/2014 | Oberholzer et al. |

FOREIGN PATENT DOCUMENTS

| WO | 2007014290 A2 | 2/2007 |
| WO | 2008013622 A2 | 1/2008 |

(Continued)

OTHER PUBLICATIONS

International Search Report from corresponding PCT/EP2013/067809, mailed Oct. 14, 2013.
Rudzki et al., "Selective Copper- or Silver-Catalyzed Decarboxylative Deuteration of Aromatic Carboxylic Acids", Synthesis 2012, 44, pp. 184-193.

(Continued)

*Primary Examiner* — Kamal Saeed
(74) *Attorney, Agent, or Firm* — Miles & Stockbridge P.C.

(57) ABSTRACT

A new process for the preparation of 3,5-bis(haloalkyl)-pyrazole derivatives of the general formula (I)

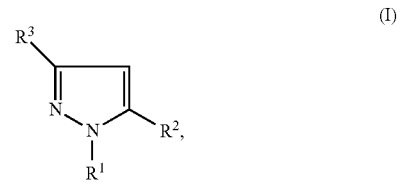

(I)

is described, resulting from the reaction of 3,5-bis(haloalkyl)-pyrazole-4-carboxylic acid derivatives of the general formula (IIa)

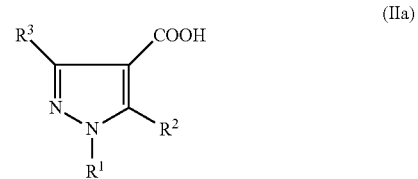

(IIa)

with a copper compound and a base at elevated temperature wherein
$R^1$ is selected from H, $C_{1-12}$-alkyl, $C_{3-8}$-cycloalkyl, $C_{6-18}$-aryl, $C_{7-19}$-arylalkyl or $C_{7-19}$-alkylaryl, $CH_2CN$, $CH_2CX_3$, $CH_2COOH$, $CH_2COO(C_{1-12})$-alkyl, and
X is independently of each other F, Cl, Br, I;
$R^2$ and $R^3$ are selected independently of each other from $C_1$-$C_6$-haloalkyl.

13 Claims, No Drawings

(56) References Cited

FOREIGN PATENT DOCUMENTS

| WO | 2008013925 | A2 | 1/2008 |
|---|---|---|---|
| WO | 2008091580 | A2 | 7/2008 |
| WO | 2008091594 | A2 | 7/2008 |
| WO | 2009055514 | A2 | 4/2009 |
| WO | 2009094407 | A2 | 7/2009 |
| WO | 2009094445 | A2 | 7/2009 |
| WO | 2009132785 | A1 | 11/2009 |
| WO | 2010/037479 | A1 | 4/2010 |
| WO | 2010/065579 | A2 | 6/2010 |
| WO | 2010/066353 | A1 | 6/2010 |
| WO | 2010123791 | A1 | 6/2010 |
| WO | 2010/149275 | A1 | 12/2010 |
| WO | 2011/051243 | A1 | 5/2011 |
| WO | 2011/076699 | A1 | 6/2011 |
| WO | 2011/085170 | A1 | 7/2011 |

OTHER PUBLICATIONS

Maggio et al., "Synthesis and induction of G0-G1 phase arrest with apoptosis of 3,5-dimethyl-6-phenyl-8(trifluoromethyl)-5,6-dihydropyrazolo [3,4-f][1,2,3,5]tetrazepin-r(3H)-one", ScienceDirect, European Journal of Medicinal Chemistry 43, (2008) pp. 2386-2394.

Guillou et al., "N-arylation of 3-alkoxypyrazoles, the case of the pyridines", Elsevier, Tetrahedron 66 (2010) pp. 2654-2663.

Tanaka, et al., "Reactions of Trifluoroacetonitrile Oxide or -nitrilimines with B-Diketones and B-Keto Esters", XP-002688704, The Chemical Society of Japan, Notes, Bull. Chem. Soc., 59, (1986), pp. 2631-2632.

Goossen et al., "Copper-Catalyzed Protodecarboxylation of Aromatic Carboxylic Acids", May 3, 2007, Adv. Synth. Catal. 2007,I 349, pp. 2241-2246, XP-002688705.

Sloop et al., "Synthesis of fluorinated heterocycles", Elsevier, Journal of Fluorine Chemistry 118 (2002), pp. 135-147.

PROCEDURE FOR THE DECARBOXYLATION OF 3,5-BIS(HALOALKYL)-PYRAZOLE-4-CARBOXYLIC ACID DERIVATIVES

CROSS REFERENCE TO RELATED APPLICATIONS

This application is a §371 National Stage Application of PCT/EP2013/067809, filed Aug. 28, 2013, which claims priority to EP 12356019.5, filed Aug. 30, 2012.

BACKGROUND

1. Field of the Invention

The present invention concerns the decarboxylation of 3,5-bis(haloalkyl)-pyrazole-4-carboxylic acid derivatives for the synthesis of 3,5-bis(haloalkyl)-pyrazole derivatives.

2. Description of Related Art 3,5-bis(haloalkyl)-pyrazole derivatives are important building blocks for the preparation of crop protection chemicals, as those described in WO 2007/014290, WO 2008/013925, WO 2008/013622, WO 2008/091594, WO 2008/091580, WO 2009/055514, WO 2009/094407, WO 2009/094445, WO 2009/132785, WO 2010/037479, WO 2010/065579, WO 2010/066353, WO 2010/123791, WO 2010/149275, WO 2011/051243, WO 2011/085170, WO 2011/076699.

Decarboxylation reactions of 4-carboxylic acid pyrazoles bearing one haloalkyl substituent are poorly developed: only two references can be found in the literature. Indeed, the resulting products are generally very volatile, thus very difficult to isolate.

5-Methyl-1-phenyl-3-(trifluoromethyl)-1H-pyrazole-4-carboxylic acid is transformed into 5-methyl-1-phenyl-3-trifluoromethyl pyrazole by reaction with copper powder in quinoline (K. Tanaka et al., *Bull. Chem. Soc. Jpn.*, 1986, 2631-2632), but the yield merely reaches 32%.

Maggio et al. describe the decarboxylation of 5-amino-1-phenyl-3-(trifluoromethyl)-1H-pyrazole-4-carboxylic acid (*Eur. J. Med. Chem.*, 2008, 2386-2394) by heating it neat at its melting point for one hour with a low yield of 30%.

No method is described for the decarboxylation of a 4-carboxylic acid pyrazole bearing more than one haloalkyl substituent.

Guillou et al. describe a copper-catalyzed protodecarboxylation on pyrazoles (*Tetrahedron* 2010, 66, 2654-2663) using $Cu_2O$ in the presence of 1,10-phenanthroline and cesium carbonate. The reaction is carried out in DMF and under harsh conditions (microwave irradiation for 2 h at 200° C.). Metal-catalyzed protodecarboxylation reactions are described by Goossen et al. (*Synthesis*, 2012, 184-193) using copper and silver catalysts. These reactions are performed on aromatic and heteroaromatic carboxylic acids, however this reaction is not shown for the substrates having bis(haloalkyl)-substituents. Bis(haloalkyl)-substituents on heteroaromatic carboxylic acids are known to effect decarboxylation reactions in a negative way (e.g. very low yield or no yield).

SUMMARY

The present invention has for objective to provide an efficient method for the decarboxylation of 3,5-bis(haloalkyl)-pyrazole-4-carboxylic acid derivatives avoiding the disadvantages of the methods described above.

Surprisingly, 3,5-bis(haloalkyl)-pyrazole derivatives of the general formula (I)

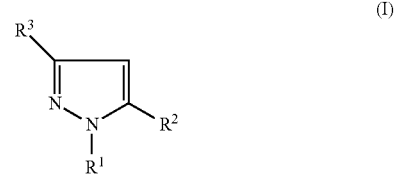

can be prepared by reacting 3,5-bis(haloalkyl)-pyrazole-4-carboxylic acid derivatives of the general formula (IIa)

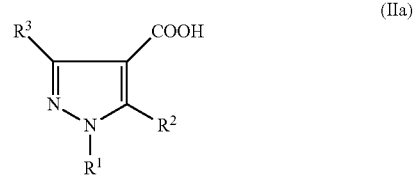

with a copper compound and a base at elevated temperature wherein $R^1$ is selected from H, $C_{1-12}$-alkyl, $C_{3-8}$-cycloalkyl, $C_{6-18}$-aryl, $C_{7-19}$-arylalkyl or $C_{7-19}$-alkylaryl, $CH_2CN$, $CH_2CX_3$, $CH_2COOH$, $CH_2COO(C_{1-12})$-alkyl, and X is independently of each other F, Cl, Br, I;

$R^2$ and $R^3$ are selected independently of each other from $C_1$-$C_6$-haloalkyl.

DETAILED DESCRIPTION OF A PREFERRED EMBODIMENT

Pyrazoles according to formula (I) can be made in good yield and purity so that the processes according to the invention overcomes the disadvantages of the processes described in the state of the art.

A preferred embodiment of the present invention relates to a process for preparing pyrazoles of formula (I), wherein $R^1$ is selected from H, $C_{1-12}$-alkyl, $CH_2CN$, $CH_2COO$—$(C_{1-12})$-alkyl, and $R^2$ and $R^3$ are selected independently of each other from $CF_3$, $CF_2H$, $CF_2Cl$.

An especially preferred embodiment of the present invention relates to a process for preparing pyrazoles of formula (I), wherein $R^1$ is selected from H, $CH_3$, $CH_2COO$—$(C_{1-12})$-alkyl, and $R^2$ and $R^3$ are selected independently of each other from $CF_3$, $CF_2H$, $CF_2Cl$.

Furthermore preferred is an embodiment of the present invention which relates to a process for preparing pyrazoles of formula (I), wherein $R^1$ is H or $CH_3$.

Furthermore preferred is an embodiment of the present invention which relates to a process for preparing pyrazoles of formula (I), wherein $R^2$ is $CF_2H$.

General Definitions

In the context of the present invention, the term "halogens" (Hal), unless defined differently, comprises those elements which are selected from the group comprising fluorine, chlorine, bromine and iodine, preferably fluorine, chlorine and bromine, more preferably fluorine and chlorine.

Optionally substituted groups may be mono- or polysubstituted, where the substituents in the case of polysubstitutions may be the same or different.

Haloalkyl: straight-chain or branched alkyl groups having 1 to 6 and preferably 1 to 3 carbon atoms (as specified above), where some or all of the hydrogen atoms in these groups may be replaced by halogen atoms as specified above, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro, 2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent, for example haloalkylaminoalkyl etc., unless defined elsewhere. Preference is given to alkyl groups substituted by one or more halogen atoms, for example trifluoromethyl ($CF_3$), difluoromethyl ($CHF_2$), $CF_3CH_2$, $CF_2Cl$ or $CF_3CCl_2$.

Alkyl groups in the context of the present invention, unless defined differently, are linear, branched or cyclic saturated hydrocarbyl groups. The definition C1-C12-alkyl encompasses the widest range defined herein for an alkyl group. Specifically, this definition encompasses, for example, the meanings of methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl or n-dodecyl.

Alkenyl groups in the context of the present invention, unless defined differently, are linear, branched or cyclic hydrocarbyl groups containing at least one single unsaturation (double bond). The definition $C_2$-$C_{12}$-alkenyl encompasses the widest range defined herein for an alkenyl group. Specifically, this definition encompasses, for example, the meanings of vinyl; allyl (2-propenyl), isopropenyl (1-methylethenyl); but-1-enyl (crotyl), but-2-enyl, but-3-enyl; hex-1-enyl, hex-2-enyl, hex-3-enyl, hex-4-enyl, hex-5-enyl; hept-1-enyl, hept-2-enyl, hept-3-enyl, hept-4-enyl, hept-5-enyl, hept-6-enyl; oct-1-enyl, oct-2-enyl, oct-3-enyl, oct-4-enyl, oct-5-enyl, oct-6-enyl, oct-7-enyl; non-1-enyl, non-2-enyl, non-3-enyl, non-4-enyl, non-5-enyl, non-6-enyl, non-7-enyl, non-8-enyl; dec-1-enyl, dec-2-enyl, dec-3-enyl, dec-4-enyl, dec-5-enyl, dec-6-enyl, dec-7-enyl, dec-8-enyl, dec-9-enyl; undec-1-enyl, undec-2-enyl, undec-3-enyl, undec-4-enyl, undec-5-enyl, undec-6-enyl, undec-7-enyl, undec-8-enyl, undec-9-enyl, undec-10-enyl; dodec-1-enyl, dodec-2-enyl, dodec-3-enyl, dodec-4-enyl, dodec-5-enyl, dodec-6-enyl, dodec-7-enyl, dodec-8-enyl, dodec-9-enyl, dodec-10-enyl, dodec-11-enyl; buta-1,3-dienyl or penta-1,3-dienyl.

Alkynyl groups in the context of the present invention, unless defined differently, are linear, branched or cyclic hydrocarbyl groups containing at least one double unsaturation (triple bond). The definition $C_2$-$C_{12}$-alkynyl encompasses the widest range defined herein for an alkynyl group. Specifically, this definition encompasses, for example, the meanings of ethynyl (acetylenyl); prop-1-ynyl and prop-2-ynyl.

Cycloalkyl: monocyclic, saturated hydrocarbyl groups having 3 to 8 and preferably 3 to 6 carbon ring members, for example (but not limited to) cyclopropyl, cyclopentyl and cyclohexyl. This definition also applies to cycloalkyl as part of a composite substituent, for example cycloalkylalkyl etc., unless defined elsewhere.

Aryl groups in the context of the present invention, unless defined differently, are aromatic hydrocarbyl groups which may have one, two or more heteroatoms selected from O, N, P and S. The definition $C_{6-18}$-aryl encompasses the widest range defined herein for an aryl group having 5 to 18 skeleton atoms, where the carbon atoms may be exchanged for heteroatoms. Specifically, this definition encompasses, for example, the meanings of phenyl, cycloheptatrienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Arylalkyl groups (aralkyl groups) in the context of the present invention, unless defined differently, are alkyl groups which are substituted by aryl groups, may have one $C_{1-8}$-alkylene chain and may have, in the aryl skeleton, one or more heteroatoms selected from O, N, P and S. The definition $C_{7-19}$-aralkyl group encompasses the widest range defined herein for an arylalkyl group having a total of 7 to 19 atoms in the skeleton and alkylene chain. Specifically, this definition encompasses, for example, the meanings of benzyl and phenylethyl.

Alkylaryl groups (alkaryl groups) in the context of the present invention, unless defined differently, are aryl groups which are substituted by alkyl groups, may have one $C_{1-8}$-alkylene chain and may have, in the aryl skeleton, one or more heteroatoms selected from O, N, P and S. The definition $C_{7-19}$-alkylaryl group encompasses the widest range defined herein for an alkylaryl group having a total of 7 to 19 atoms in the skeleton and alkylene chain. Specifically, this definition encompasses, for example, the meanings of tolyl or 2,3-, 2,4-, 2,5-, 2,6-, 3,4- or 3,5-dimethylphenyl.

The term intermediate used in the context of the present invention describes the substances which occur in the process according to the invention and are prepared for further chemical processing and are consumed or used therein in order to be converted to another substance. The intermediates can often be isolated and intermediately stored or are used without prior isolation in the subsequent reaction step. The term "intermediate" also encompasses the generally unstable and short-lived intermediates which occur transiently in multistage reactions (staged reactions) and to which local minima in the energy profile of the reaction can be assigned.

The inventive compounds may be present as mixtures of any different isomeric forms possible, especially of stereoisomers, for example E and Z isomers, threo and erythro isomers, and optical isomers, but if appropriate also of tautomers. Both the E and the Z isomers are disclosed and claimed, as are the threo and erythro isomers, and also the optical isomers, any mixtures of these isomers, and also the possible tautomeric forms.

Process Description

Scheme 1: Synthesis of 3,5-bis(haloalkyl)-pyrazole derivatives from 3,5-bis(haloalkyl)-pyrazole-4-carboxylic acid derivatives

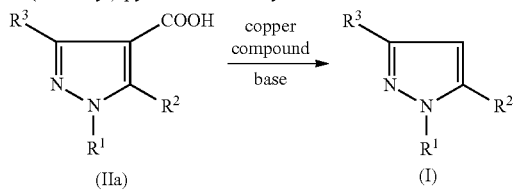

The decarboxylation step is performed in the presence of a copper compound, a base, optionally water and optionally solvent.

The copper compound is selected from Cu, $Cu_2O$, CuO, CuCl, CuI; preferred are Cu and $Cu_2O$.

The amount of copper compound can vary within a large range; preferably it is within 0.01 and 1 equivalents for 1 equivalent of of pyrazolic acid; more preferably between 0.05 to 0.5 equivalents; most preferably are 0.05 equivalents.

The base used for the process according to the invention is an organic or inorganic base. A single compound or a mixture of different compounds can be used as base. The inorganic base is selected from a group comprising cesium carbonate and potassium carbonate The organic base is selected from a group comprising quinoline, pyridines, alkylpyridines, phenanthroline, N-methylmorpholine, NMP, DMF, dimethylacetamid. Preference is given to using organic bases. Preference is also given to using a mixture of bases. Especially preferred is a mixture of organic bases.

The mixtures of organic bases are for instance binary mixtures, ternary mixtures and quaternary mixtures. Ternary mixtures are for instance 1,10-phenanthroline, NMP and quinoline; 1,10-phenanthroline, pyridine and NMP; 1,10-phenanthroline, DMF and pyridine; 1,10-phenanthroline, quinoline and pyridine; 1,10-phenanthroline, quinoline and DMF; 1,10-phenanthroline, N-methylmorpholine and quinoline; 1,10-phenanthroline N-methylmorpholine and DMF; 1,10-phenanthroline, N-methylmorpholine and pyridine. Binary mixtures are for instance 1,10-phenanthroline and NMP; 1,10-phenanthroline and pyridine; 1,10-phenanthroline and DMF; 1,10-phenanthroline and quinoline; 1,10-phenanthroline and N-methylmorpholine; 1,10-phenanthroline and alkylpyridines; 1,10-phenanthroline and dimethylacetamid.

Preferred are ternary mixtures of organic bases. Preferred is a mixture of 1,10-phenanthrolin, quinoline and NMP.

For the ternary mixtures of organic bases the volume ratio between any two compounds, independently of each other, is from 100:1 to 1:100, preferably from 50:1 to 1:50, more preferably, 25:1 to 1:25 and most preferably 15:1 to 1:15.

Further volume ratio between any two compounds of the ternary mixtures of organic bases, independently of each other, which can be used according to the present invention with increasing preference in the order given are 100:1 to 1:100, 90:1 to 1:90, 80:1 to 1:80, 70:1 to 1:70, 60:1 to 1:60, 40:1 to 1:40, 30:1 to 1:30, 10:1 to 1:10, 5:1 to 1:5.

A preferred volume ratio for the ternary mixture of organic bases is 1:50:50 to 1:1:1; more preferred is 1:5:20 to 1:5:5.

Especially preferred is a volume ratio for the mixture of 1,10-phenanthroline (A), quinoline (B) and NMP (C) of 1:5:20 to 1:5:5 ((A):(B):(C)).

The amount of organic base can vary within a large range; preferably it is within 0.1 and 30 equivalents for 1 equivalent of pyrazolic acid; more preferably between 0.5 to 10 equivalents. Most preferably are 6 equivalents of organic base.

The reaction time of the process according to the invention is generally not of critical importance and can depend on the reaction volume; preferably it is within the range of 3 to 12 h.

The temperature of the process according to the invention is ranging from 40 to 190° C.; preferably from 60° C. to 180° C., more preferably from 80° C. to 175° C.

Optionally a solvent is used for the decarboxylation reaction according to the invention. The solvent is for instance mesitylene or dichlorobenzene. The amount of solvent can vary within a large range; preferably it is within 0.1 to 40 equivalents for 1 equivalent of pyrazolic acid; more preferably between 0.2 to 20 equivalents. Most preferably the reaction according to the invention is performed without additional solvent.

Optionally water is used for the decarboxylation reaction according to the invention. The amount of water can vary within a large range; preferably it is within 0.001 and 0.1 equivalents for 1 equivalent of pyrazolic acid, more preferably between 0.02 to 0.08 equivalents.

Decarboxylation can also be performed under acidic conditions. Preferred acids for this step are: $H_2SO_4$, HCl, HBr, HI, $CH_3COOH$, $CF_3COOH$, $CF_3SO_3H$, $CH_3SO_3H$, p-toluenesulfonic acid, oleum, HF. The amount of acid can vary within a large range; preferably it is within 0.1 and 1.5 equivalents, more preferably between 0.5 to 1.2 equivalents for 1 equivalent of pyrazolic acid. Acidic decarboxylation proceeds preferably in water. The acidic decarboxylation is performed at a temperature ranging from 50 to 220° C., preferably at a temperature ranging from 70° C. to 210° C., more preferably from 80° C. to 190° C. The reaction time is generally not of critical importance and can depend on the reaction volume; preferably it is within the range of 2 to 7 h.

Decarboxylation can also be performed under basic conditions. Preferred inorganic bases are LiOH, KOH, NaOH, $K_2CO_3$, $Cs_2CO_3$, $Ba(OH)_2$, $NH_4OH$, n-BuONa. Especially preferred bases are $K_2CO_3$ and $Cs_2CO_3$. The amount of base can vary within a large range; preferably it is within 0.1 and 1.5 equivalents, more preferably between 0.5 to 1 equivalents for 1 equivalent of of pyrazolic acid. The basic decarboxylation is performed at a temperature ranging from 40 to 150° C., preferably at a temperature ranging from 50° C. to 140° C., more preferably from 80° C. to 120° C. The reaction time is generally not of critical importance and can depend on the reaction volume; preferably it is within the range of 1 to 7 h. Optionally the decarboxylation under basic conditions can be performed in the presence of high boiling solvents like NMP, quinoline, dimethylacetamid, 1,10-phenanthrolin or mesitylene.

3,5-bis(haloalkyl)pyrazoles of the formula (II)

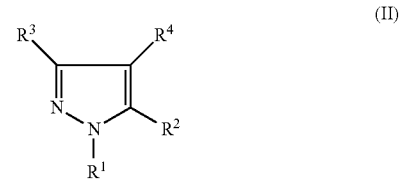

in which $R^1$ is selected from H, $C_{1-12}$-alkyl, $C_{3-8}$-cycloalkyl, $C_{6-18}$-aryl, $C_{7-19}$-arylalkyl or $C_{7-19}$-alkylaryl, $CH_2CN$, $CH_2CX_3$, $CH_2COOH$, $CH_2COO$—$(C_{1-12})$-alkyl and X is independently of each other F, Cl, Br, I, $R^2$ and $R^3$ are selected independently of each other from $C_1$-$C_6$-haloalkyl groups, $R^4$ is selected from H, Hal, COOH, (C=O)OR$^5$, CN and (C=O)NR$^5$R$^6$, where $R^5$ and $R^6$ are selected independently of each other from $C_{1-12}$-alkyl, $C_{3-8}$-cycloalkyl, $C_{6-18}$-aryl, $C_{7-19}$-arylalkyl and $C_{7-19}$-alkylaryl, or $R^5$ and $R^6$ form together with the nitrogen atom to which they are bonded a five- or six-membered ring can be prepared as follows:

In step A), α,α-dihaloamines of the formula (III),

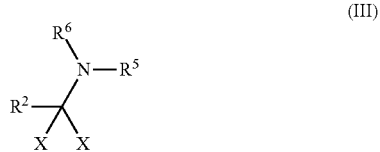

(III)

in which X is Cl or F and $R^2$, $R^5$ and $R^6$ are as described above, are reacted with compounds of the formula (IV),

(IV)

in which the radicals are each as defined above and, in step B), the product is reacted with hydrazines of the formula (V),

(V)

in which $R^1$ is as defined above.

Scheme 2: Preparation of 3,5-bis(haloalkyl)pyrazoles of the formula (II)

Step A)

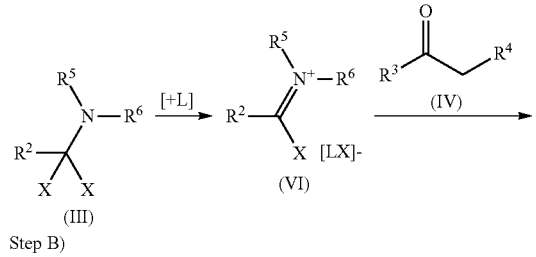

Step B)

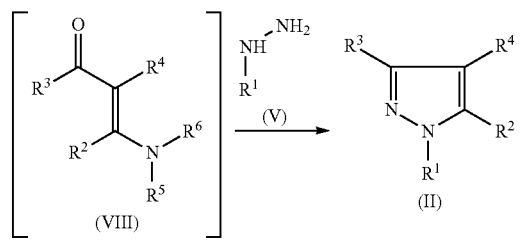

In step A), α,α-dihaloamines of the formula (III) are reacted, optionally in the presence of a Lewis acid [L], with compounds of the formula (IV).

Compounds of the general formula (III) are e.g. 1,1,2,2-tetrafluoroethyl-N,N-dimethylamine (TFEDMA), 1,1,2,2-tetrafluoroethyl-N,N-diethylamine, 1,1,2-trifluoro-2-(trifluoromethyl)ethyl-N,N-dimethylamine, 1,1,2-trifluoro-2-(trifluoromethyl)ethyl-N,N-diethylamine (Ishikawa's reagent), 1,1,2-trifluoro-2-chloroethyl-N,N-dimethylamine and 1,1,2-trifluoro-2-chloroethyl-N,N-diethylamine (Yarovenko's reagent).

Compounds of the general formula (III) are used as aminoalkylating agents. α,α-Dihaloamines such as TFEDMA and Ishikawa's reagent are commercially available or can be prepared (cf. Yarovenko et al., Zh. Obshch. Khim. 1959, 29, 2159, Chem. Abstr. 1960, 54, 9724h or Petrov et al., J. Fluor. Chem. 109 (2011) 25-31).

The α,α-dihaloamine is first reacted with Lewis acid [L], for example $BF_3$, $AlCl_3$, $SbCl_5$, $SbF_5$, $ZnCl_2$, and then the mixture of the compound of the formula (IV) and a base is added, in substance or dissolved in a suitable solvent (cf. WO 2008/022777).

The reaction is effected at temperatures of −20° C. to +40° C., preferably at temperatures of −20° C. to +30° C., more preferably at −10 to 20° C. and under standard pressure. Due to the hydrolysis sensitivity of the α,α-dihaloamines, the reaction is conducted in anhydrous apparatuses under inert gas atmosphere.

The reaction time is not critical and may, according to the batch size and temperature, be selected within a range between a few minutes and several hours.

1 mol of the Lewis acid [L] is reacted with equimolar amounts of the α,α-dihaloamine of the formula (III).

The aminoalkylation (reaction with compound of the formula (III)) is preferably effected in the presence of a base. Preference is given to organic bases such as trialkylamines, pyridines, alkylpyridines, phosphazenes and 1,8-diazabicyclo[5.4.0]undecene (DBU); alkali metal hydroxides, for example lithium hydroxide, sodium hydroxide or potassium hydroxide, alkali metal carbonates ($Na_2CO_3$, $K_2CO_3$) and alkoxides, for example NaOMe, NaOEt, NaOt-Bu, KOt-Bu or KF.

1 mol of the base for the compound of the formula (IV) is reacted with equimolar amounts of the α,α-dihaloamine of the formula (III).

Preference is given to using keto compounds of the formula (IV) selected from the group comprising ethyl 4,4,4-trifluoro-3-oxobutanoates, methyl 4,4,4-trifluoro-3-oxobutanoates, ethyl 4,4-difluoro-3-oxobutanoates, ethyl 4-chloro-4,4-difluoro-3-oxobutanoates, 1,1,1-trifluoroacetone or 4-chloro-4,4-difluoro-3-oxobutanenitriles.

Said keto compounds of the formula (IV) are commercially available or can be prepared according to procedures described in the literature.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane. Particular preference is given, for example, to THF, acetonitriles, ethers, toluene, xylene, chlorobenzene, n-hexane, cyclohexane or methylcyclohexane, and very particular preference, for example, to acetonitrile, THF, ether or dichloromethane.

The intermediates of the formula (VII) are used in the cyclization step B) with hydrazines of the general formula (V) without prior workup.

Alternatively, the intermediates of the formula (VII) can be isolated and characterized by suitable workup steps and optionally further purification.

The cyclization in step B) is effected at temperatures of −40° C. to 80° C., preferably at temperatures of −10° C. to 60° C., more preferably at −10° C. to 50° C. and under standard pressure.

The reaction time is not critical and may, according to the batch size, be selected within a relatively wide range.

Typically, the cyclization step B) is effected without changing the solvent.

1 to 2 mol, preferably 1 to 1.5, of the hydrazines of the formula (V) per 1 mol of the compound of the formula (IV) are used.

Preference is given to performing all reaction steps of the process in the same solvent.

Said hydrazines of the formula (V) are commercially available or can be prepared as described, for example, in Niedrich et al., Journal fuer Praktische Chemie (Leipzig) (1962), 17 273-81; Carmi, A.; Pollak, Journal of Organic Chemistry (1960), 25 44-46.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; alcohols such as methanol, ethanol, isopropanol or butanol, nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane. Particular preference is given, for example, to acetonitrilestoluene, xylene, chlorobenzene, n-hexane, cyclohexane or methylcyclohexane, and very particular preference, for example, to acetonitriles, THF, toluene or xylene. After the reaction has ended, for example, the solvents are removed and the product is isolated by filtration, or the product is first washed with water and extracted, the organic phase is removed and the solvent is removed under reduced pressure.

The compounds of the formula (II) where $R^4$=$COOR^5$ can then be converted to pyrazole acids of the formula (IIa) $R^4$=COOH.

The conversion is generally performed under acidic or basic conditions.

For acidic hydrolysis, preference is given to mineral acids, for example $H_2SO_4$, HCl, $HSO_3Cl$, HF, HBr, HI, $H_3PO_4$ or organic acids, for example $CF_3COOH$, p-toluenesulphonic acid, methanesulphonic acid, trifluoromethanesulphonic acid. The reaction can be accelerated by the addition of catalysts, for example $FeCl_3$, $AlCl_3$, $BF_3$, $SbCl_3$, $NaH_2PO_4$. The reaction can likewise be performed without addition of acid, only in water.

Basic hydrolysis is effected in the presence of inorganic bases such as alkali metal hydroxides, for example lithium hydroxide, sodium hydroxide or potassium hydroxide, alkali metal carbonates, for example $Na_2CO_3$, $K_2CO_3$ and alkali metal acetates, for example NaOAc, KOAc, LiOAc, and alkali metal alkoxides, for example NaOMe, NaOEt, NaOt-Bu, KOt-Bu of organic bases such as trialkylamines, alkylpyridines, phosphazenes and 1,8-diazabicyclo[5.4.0]undecene (DBU). Preference is given to the inorganic bases, for example NaOH, KOH, $Na_2CO_3$ or $K_2CO_3$.

The process step is performed preferably within a temperature range from 20° C. to 150° C., more preferably at temperatures of 30° C. to 110° C., most preferably at 30° C. to 80° C.

The process step is generally performed under standard pressure. Alternatively, however, it is also possible to work under vacuum or under elevated pressure (for example reaction in an autoclave with aqueous HCl).

The reaction time may, according to the batch size and the temperature, be selected within a range between 1 hour and several hours.

The reaction step can be performed in substance or in a solvent. Preference is given to performing the reaction in a solvent. Suitable solvents are, for example, selected from the group comprising water, alcohols such as methanol, ethanol, isopropanol or butanol, aliphatic and aromatic hydrocarbons, for example n-hexane, benzene or toluene, which may be substituted by fluorine and chlorine atoms, such as methylene chloride, dichloroethane, chlorobenzene or dichlorobenzene; ethers, for example diethyl ether, diphenyl ether, methyl tert-butyl ether, isopropyl ethyl ether, dioxane, diglyme, dimethylglycol, dimethoxyethane (DME) or THF; nitriles such as methyl nitrile, butyl nitrile or phenyl nitrile; amides we dimethylformamide (DMF) or N-methylpyrrolidone (NMP) or mixtures of such solvents, particular preference being given to water, acetonitrile, dichloromethane and alcohols (ethanol).

EXAMPLES

Example 1

3-(difluoromethyl)-1-methyl-5-(trifluoromethyl)-1H-pyrazole

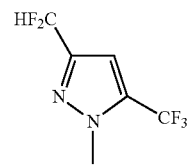

3-(difluoromethyl)-1-methyl-5-(trifluoromethyl)-1H-pyrazole-4-carboxylic acid (8.60 mmol, 2.1 g), $Cu_2O$ (65 mg, 0.45 mmol), 1,10-Phenanthrolin (176 mg, 0.90 mmol) and NMP (15 mL), quinoline (5 mL) and $H_2O$ (2 drops) were heated for 10 h at 160° C. The reaction mixture was diluted with water and the product extracted three times with diethyl ether. The organic phase was washed with 1M HCl-solution. The organic phase was dried and the solvent removed under atmospheric pressure with Vigreux Colummn. The product N-Methyl-5-trifluormethyl-3-difluoromethylpyrazol (0.85 g, 4.25 mmol, 50%) was purified via distillation in vacuum, (b.p.: 45-46° C./27 mbar).

$^1$H NMR ($CDCl_3$, 300 MHz, 25° C.): δ=6.84 (s, 1H), 6.66 (t, 1H, $CHF_2$, $J_{H-F}$=55 Hz), 4.02 (s, 3H, N—$CH_3$) ppm.

$^{13}$C NMR (CDCl$_3$, 75 MHz, 25° C.): δ=145.6 (t, J$_{C-F}$=30 Hz), 133.3 (q, J$_{C-F}$=39.6 Hz), 119.5 (q, CF$_3$, J$_{C-F}$=267.2 Hz), 110.3 (t, CHF$_2$, J$_{C-F}$=233.2 Hz), 105.2 (q, J$_{C-F}$=2 Hz), 38.3 (q, N—CH3, J$_{C-F}$=1.6 Hz) ppm.

$^{19}$F NMR (CDCl$_3$, 282 MHz, 25° C.): δ=−61.5 (CF$_3$), −113.0 (CHF$_2$) ppm.

Examples 2 to 7 were all prepared according to the protocol of Example 1.

Example 2

3,5-bis(difluoromethyl)-1-methyl-1H-pyrazole

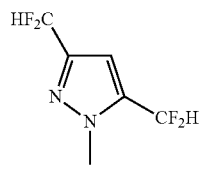

Yield 78%, oil, b.p.=78-80° C., 28 mbar.

$^1$H NMR (CDCl$_3$, 300 MHz, 25° C.): δ=6.73 (t, 1H, CHF$_2$, J$_{H-F}$=53.4 Hz), 6.69 (s, 1H), 6.66 (t, 1H, CHF$_2$, J$_{H-F}$=54.9 Hz), 4.01 (s, 3H, N—CH$_3$) ppm.

$^{13}$C NMR (CDCl$_3$, 75 MHz, 25° C.): δ=145.6 (t, J$_{C-F}$=30 Hz), 136.5 (t, J$_{C-F}$=26.6 Hz), 110.6 (t, CHF$_2$, J$_{C-F}$=234.1 Hz), 108.2 (t, CHF$_2$, J$_{C-F}$=236.5 Hz), 104.7 (m), 38.1 (s, N—CH$_3$) ppm.

$^{19}$F NMR (CDCl$_3$, 282 MHz, 25° C.): δ=−112.5 (CHF$_2$, J$_{F-H}$=54.9 Hz), −113.7 (CHF$_2$, =53.3 Hz) ppm.

Example 3

3-(difluoromethyl)-1-methyl-5-(pentafluoroethyl)-1H-pyrazole

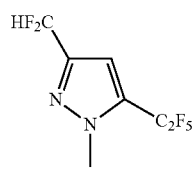

Yield 63%. Oil, b.p.=53-54° C., 28 mbar.

$^1$H NMR (CDCl$_3$, 300 MHz, 25° C.): δ=6.84 (s, 1H, Harom), 6.67 (t, 1H, CHF$_2$, J$_{H-F}$=54.8 Hz), 4.05 (s, 3H, N—CH$_3$) ppm.

$^{13}$C NMR (CDCl$_3$, 75 MHz, 25° C.): δ=146.0 (t, J$_{C-F}$=30.1 Hz), 131.2 (t, J$_{C-F}$=28.9 Hz), 118.5 (qt, CF$_2$—CF$_3$, J$^1_{C-F}$=285.7 Hz, J$^2_{C-F}$=37.3 Hz), 110.2 (t, CHF$_2$, J$_{C-F}$=234.8 Hz), 109.8 (tq, CF$_2$—CF$_3$, J$^1_{C-F}$=252.7 Hz, J$^2_{C-F}$=40.6 Hz), 106.9 (brs), 39.2 (brs, N—CH$_3$) ppm.

$^{19}$F NMR (CDCl$_3$, 282 MHz, 25° C.): δ=−84.4 (CF$_2$CF$_3$), −111.1 (CF$_2$CF$_3$), −113.0 (CHF$_2$, J$_{F-H}$=54.8 Hz) ppm.

Example 4

3-(difluoromethyl)-1-phenyl-5-(pentafluoroethyl)-1H-pyrazole

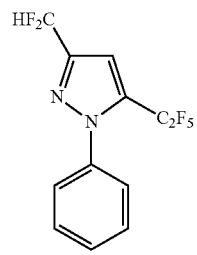

Yield 88%, isolated via column chromatographie on SiO$_2$ using Pentane/Et$_2$O 95:5 mixture.

$^1$H NMR (CDCl$_3$, 300 MHz, 25° C.): δ=7.54-7.43 (m, 5H), 7.03 (brs, 1H), 6.76 (t, 1H, CHF$_2$, J$_{H-F}$=54.6 Hz) ppm.

$^{13}$C NMR (CDCl$_3$, 75 MHz, 25° C.): δ=147.4 (t, J$_{C-F}$=30.4 Hz), 139.1 (s,), 132.4 (t, J$_{C-F}$=28.1 Hz), 130.2 (s,), 129.1 (s, CHphenyl), 126.7 (s), 118.5 (qt, CF$_2$—CF$_3$, J$^1_{C-F}$=286.3 Hz, J$^2_{C-F}$=36.8 Hz), 110.4 (t, CHF$_2$, J$_{C-F}$=235.3 Hz), 109.5 (tq, CF$_2$—CF$_3$, J$^1_{C-F}$=252.0 Hz, J$^2_{C-F}$=40.4 Hz), 107.5 (brs) ppm.

$^{19}$F NMR (CDCl$_3$, 282 MHz, 25° C.): δ=−83.9 (CF$_2$CF$_3$), −107.1 (CF$_2$CF$_3$), −113.0 (CHF$_2$, J$_{F-H}$=54.6 Hz) ppm.

Example 5

3-(difluoromethyl)-1-phenyl-5-(trifluoromethyl)-1H-pyrazole

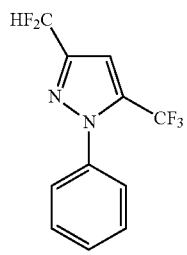

Yield 84%, isolated via column chromatographie on SiO$_2$ using Pentan/Et$_2$O 95:5 mixture.

$^1$H NMR (CDCl$_3$, 300 MHz, 25° C.): δ=7.55-7.48 (m, 5H), 7.07 (brs, 1H), 6.78 (t, 1H, CHF$_2$, J$_{H-F}$=54.6 Hz) ppm.

$^{13}$C NMR (CDCl$_3$, 75 MHz, 25° C.): δ=146.9 (t, J$_{C-F}$=30.5 Hz), 138.4 (s), 134.2 (q, J$_{C-F}$=40.0 Hz), 130.0 (s,), 129.3 (s, CH), 125.7 (s, CH), 119.2 (q, CF$_3$, J$_{C-F}$=269.4 Hz), 110.4 (t, CHF$_2$, J$_{C-F}$=235.1 Hz, 106.4 (brs, CH pyrazol) ppm.

$^{19}$F NMR (CDCl$_3$, 282 MHz, 25° C.): δ=−58.4 (CF$_3$), −112.9 (CHF$_2$, J$_{F-H}$=54.6 Hz) ppm.

Example 6

1-tert-butyl-3-(difluoromethyl)-5-(trifluoromethyl)-1H-pyrazole

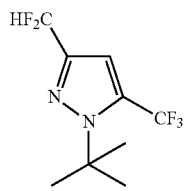

Yield 83%, oil, b.p.=68-69° C., 32 mbar.

$^1$H NMR (CDCl$_3$, 300 MHz, 25° C.): δ=6.94 (brs, 1H, Harom), 6.68 (t, 1H, CHF$_2$, J$_{H\text{-}F}$=54.8 Hz), 1.69 (s, 9H, CH$_3$) ppm.

$^{13}$C NMR (CDCl$_3$, 75 MHz, 25° C.): δ=143.5 (t, J$_{C\text{-}F}$=30.4 Hz), 132.7 (q, J$_{C\text{-}F}$=40.1 Hz), 119.9 (q, CF$_3$, J$_{C\text{-}F}$=268.9 Hz), 110.8 (t, CHF$_2$, J$_{C\text{-}F}$=233.9 Hz), 108.0 (q, J$_{C\text{-}F}$=3.8 Hz), 64.2 (s, tBu), 29.8 (q, tBuCH$_3$, J$_{C\text{-}F}$=2.1 Hz) ppm.

$^{19}$F NMR (CDCl$_3$, 282 MHz, 25° C.): δ=−55.6 (CF$_3$), −112.3 (CHF$_2$, J$_{F\text{-}H}$=54.9 Hz) ppm.

Example 7

3-(difluoromethyl)-5-(pentafluoroethyl-1H-pyrazole

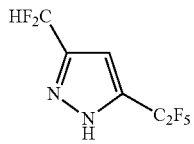

The N—H-5-pentafluoroethyl-3-difluoromethylpyrazol, yield 44%, Oil b.p.=63-65° C., 55 mbar.

$^1$H NMR (CDCl$_3$, 300 MHz, 25° C.): δ=11.87 (brs, 1H, NH), 6.87 (brs, 1H), 6.80 (t, 1H, CHF$_2$, J$_{H\text{-}F}$=54.7 Hz) ppm.

$^{13}$C NMR (CDCl$_3$, 75 MHz, 25° C.): δ=141.5 (brs, C$_{IV}$arom), 139.5 (brs, C$_{IV}$arom), 118.4 (qt, CF$_2$—CF$_3$, J$^1_{C\text{-}F}$=285.4 Hz, J$^2_{C\text{-}F}$=37.3 Hz), 109.9 (tq, CF$_2$—CF$_3$, J$^1_{C\text{-}F}$=252.2 Hz, J$^2_{C\text{-}F}$=40.1 Hz), 108.4 (t, CHF$_2$, J$_{C\text{-}F}$=238.2 Hz), 104.9 (brs, CHpyrazol) ppm.

$^{19}$F NMR (CDCl$_3$, 282 MHz, 25° C.): δ=−85.1 (CF$_2$CF$_3$), −113.5 (CF$_2$CF$_3$), −113.8 (CHF$_2$, J$_{F\text{-}H}$=54.7 Hz) ppm.

Example 8

3-(difluoromethyl)-5-(trifluoromethyl)-1H-pyrazole

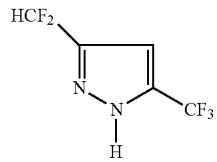

A mixture of N-tert-butyl-3-(difluoromethyl)-5-(trifluoromethyl) pyrazole (0.10 g, 0.41 mmol), anisole (0.13 g, 0.14 ml, 1.23 mmol) and trifluoroacetic acid (2 ml) was stirred and heated to 90° C. for 16 h. The reaction mixture was cooled to ambient temperature, neutralised by the addition of a solution of sodium sodium hydroxide (210 mmol, 8.4 g) in water (30 mL) until the pH=8. The aqueous layer was extracted with diethyl ether (3×30 mL). The combined organic layers were washed with brine (30 mL), dried over sodium sulphate and the solvent was evaporated at atmospheric pressure. The crude material was purified by column chromatography on silica gel with pentane/diethyl ether (gradient 100:0 to 50:50) as eluent to afford pure N—H-3-(difluoromethyl)-5-(trifluoromethyl) pyrazole (0.47 g, 2.53 mmol, 76%) as a colourless solid.

$^1$H NMR (CDCl$_3$, 300 MHz, 25° C.): δ=13.38 (brs, 1H, N—H), 6.84 (s, 1H, Harom), 6.79 (t, 1H, CHF$_2$, J$_{H\text{-}F}$=54.7 Hz) ppm.

$^{13}$C NMR (CDCl$_3$, 75 MHz, 25° C.): δ=141.1 (brs, C$_{IV}$arom, C$^1$ and C$^3$), 120.1 (q, CF$_3$, J$_{C\text{-}F}$=268.8 Hz), 108.3 (t, CHF$_2$, J$_{C\text{-}F}$=238.2 Hz), 103.6 (d, CHarom, J$_{C\text{-}F}$=1.6 Hz) ppm.

Example 9

N-Methyl-3-difluoromethyl-5-trifluoromethyl-4-pyrazolecarboxylic acid ethyl ester

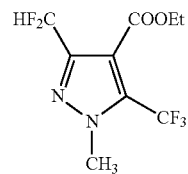

BF$_3$.OEt$_2$ (0.62 ml, 5.0 mmol) was added to a solution of TFEDMA (0.59 ml, 5.0 mmol) in dry dichloromethanes (5 ml) under argon in a Teflon flask. The solution was stirred at room temperature for 15 min, before the dichloromethane was removed under reduced pressure. The residue was then taken up in dry acetonitrile (5 ml). In a second Teflon flask, ethyl trifluoroacetoacetate (0.73 ml, 5.0 mmol) was added to a solution of potassium fluoride (0.88 g, 15.0 mmol) in dry acetonitrile (10 ml) and the mixture was stirred at room temperature for 15 min. To this were added dropwise, at −30° C., the contents of the first flask. The reaction mixture was brought to room temperature in the cold bath and stirred overnight. Methyl hydrazine (0.32 ml, 6.0 mmol) was then added dropwise at room temperature and the mixture was stirred overnight. The solvent was removed under reduced pressure and the residue was purified by flash chromatography on silica gel with a pentanes/diethyl ether mixture (9:1-8:2). N-Methyl-5-trifluoromethyl-3-difluoromethyl-4-pyrazolecarboxylic acid ethyl ester (0.99 g, 3.64 mmol, 73%) was obtained as a yellow oil.

$^1$H NMR (CDCl$_3$, 300 MHz, 25° C.): δ=7.00 (t, 1H, CHF$_2$, J$_{H\text{-}F}$=54 Hz), 4.37 (q, 2H, CH$_2$, J=7.2 Hz), 4.12 (s. 3H, N—CH$_3$), 1.37 (t, 3H, CH$_3$, J=7.2 Hz) ppm. $^{13}$C NMR (CDCl$_3$, 75 MHz, 25° C.): δ=160.2 (CO), 145.7 (t, C$_{IV}$arom, J$_{C\text{-}F}$=25.6 Hz), 133.2 (q, C$_{IV}$arom, J$_{C\text{-}F}$=40.3 Hz), 119.0 (q, CF$_3$, J$_{C\text{-}F}$=271.2 Hz), 114.4 (C$_{IV}$arom), 109.0 (t, CHF$_2$, J$_{C\text{-}F}$=237.9 Hz), 61.9 (CH$_2$), 40.8 (q, N—CH$_3$, J$_{C\text{-}F}$=3.2 Hz), 13.8 (CH$_3$) ppm. $^{19}$F NMR (CDCl$_3$, 282 MHz, 25° C.): δ=−57.6 (CF$_3$), −116.4 (CHF$_2$) ppm.

Example 10

N-Methyl-3-difluoromethyl-5-trifluoromethyl-4-pyrazolecarboxylic acid

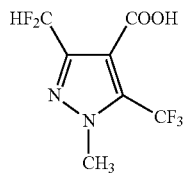

N-Methyl-5-trifluoromethyl-3-difluoromethyl-4-pyrazolecarboxylic acid ethyl ester (0.5 g, 1.84 mmol) in ethanol (3 ml) was admixed gradually with an 8N aqueous sodium hydroxide solution (0.7 ml) and stirred at room temperature for 3 h. The solvent was removed by rotary evaporation; the residue was taken up in water (10 ml) and extracted with diethyl ether (10 Acidification to pH 1 with 1M HCl was followed by extraction with ethyl acetate (3×10 ml). The combined organic phases were dried over sodium sulphate and filtered, and the solvent was removed by rotary evaporation. N-Methyl-3-difluoromethyl-5-trifluoromethyl-4-pyrazolecarboxylic acid (0.44 g, 1.80 mmol, 98%) was isolated as a yellowish solid.

$^1$H NMR (CDCl$_3$, 300 MHz, 25° C.): δ=7.08 (t, 1H, CHF$_2$, $J_{H\text{-}F}$=53.5 Hz) 4.16 (s, 3H, N—CH$_3$) ppm.
$^{13}$C NMR (CDCl$_3$, 75 MHz, 25° C.): δ=165.5 (CO), 146.7 (t, C$_{IV}$arom, C$_{C\text{-}F}$=18.8 Hz), 134.4 (q, C$_{IV}$arom, $J_{C\text{-}F}$=30.8 Hz), 118.8 (q, CF$_3$, $J_{C\text{-}F}$7=202.5 Hz), 112.9 (C$_{IV}$arom), 108.7 (t, CHF$_2$, $J_{C\text{-}F}$=177.0 Hz), 41.1 (q, N—CH$_3$, $J_{C\text{-}F}$=2.3 Hz) ppm. $^{19}$F NMR (CDCl$_3$, 282 MHz, 25° C.): δ=−57.9 (CF$_3$), −117.3 (CHF$_2$, $J_{F\text{-}H}$=53.5 Hz) ppm.

Example 11

N—H-3-Difluoromethyl-5-trifluoromethyl-4-pyrazolecarboxylic acid ethyl ester

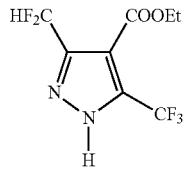

BF$_3$.OEt$_2$ (0.31 ml, 2.5 mmol) was added to a solution of TFEDMA (0.30 ml, 2.5 mmol) in dry dichloromethanes (2.5 ml) under argon in a Teflon flask. The solution was stirred at room temperature for 15 min, before the dichloromethane was removed under reduced pressure. The residue was then taken up in dry acetonitrile (2.5 ml). In a second Teflon flask, ethyl trifluoroacetoacetate (0.37 ml, 2.5 mmol) was added to a solution of potassium fluorides (0.44 g, 7.5 mmol) in dry acetonitrile (5 ml) and the mixture was stirred at room temperature for 15 min. To this were added dropwise, at −30° C., the contents of the first flask. The reaction mixture was brought to room temperature in the cold bath and stirred overnight. Hydrazine hydrate (0.15 ml, 3.0 mmol) was then added dropwise at room temperature and the mixture was stirred for 24 h. The solvent was removed under reduced pressure and the residue was purified by flash chromatography on silica gel with a pentanes/diethyl ether mixture (9:1-7:3). N—H-3-Difluoromethyl-5-trifluoromethyl-4-pyrazolecarboxylic acid ethyl ester (0.48 g, 1.88 mmol, 75%) was obtained as a yellowish oil, which crystallized when left to stand.

$^1$H NMR (CDCl$_3$, 300 MHz, 25° C.): δ=11.07 (brs, 1H, NH), 7.22 (t, 1H, CHF$_2$, $J_{H\text{-}F}$=53.5 Hz), 4.39 (q, 2H, CH$_2$, J=6.9 Hz), 1.38 (t, 3H, CH$_2$, J=6.9 Hz) ppm. $^{13}$C NMR (CDCl$_3$, 75 MHz, 25° C.): δ=160.4 (CO), 142.2 (t. C$_{IV}$arom, $J_{C\text{-}F}$=18.3 Hz), 142.2 (q, C$_{IV}$arom, $J_{C\text{-}F}$=32.0 Hz), 119.7 (q, CF$_3$, $J_{C\text{-}F}$=268.1 Hz), 111.7 (C$_{IV}$arom), 107.4 (t, CH$_2$, $J_{C\text{-}F}$=237.5 Hz), 62.0 (CH$_2$), 13.7 (CH$_3$) ppm. $^{19}$F NMR (CDCl$_3$, 282 MHz, 25° C.): δ=−62.5 (CF$_3$), −117.1 (CHF$_2$, $J_{F\text{-}H}$=53.5 Hz) ppm.

Example 12

N-Methyl-3,5-difluoromethyl-4-pyrazolecarboxylic acid ethyl ester

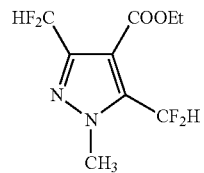

BF$_3$.OEt$_2$ (1.24 ml, 10.0 mmol) was added to a solution of TFEDMA (1.20 ml, 10.0 mmol) in dry dichloromethanes (10 ml) under argon in a Teflon flask. The solution was stirred at room temperature for 15 min, before the dichloromethane was removed under reduced pressure. The residue was then taken up in dry acetonitrile (10 ml). In a second Teflon flask, ethyl 4,4-difluoroacetoacetate (1.03 ml, 10.0 mmol) was added to a solution of pyridine (1.6 ml, 20.0 mmol) in dry acetonitrile (20 ml) and the mixture was stirred at room temperature for 15 min. To this were added dropwise, at −30° C., the contents of the first flask. The reaction mixture was brought to room temperature in the cold bath and stirred overnight. Methyl hydrazine (0.79 ml, 15.0 mmol) was then added dropwise at room temperature and the mixture was stirred overnight. The solvent was removed under reduced pressure and the residue was purified by flash chromatography on silica gel with a pentanes/diethyl ether mixture (10:0-8:2). (10:0 to 8:2). N-Methyl-3,5-difluoromethyl-4-pyrazolecarboxylic acid ethyl ester (1.75 g, 6.89 mmol, 69%) was obtained as a colourless oil, which crystallized when left to stand.

$^1$H NMR (CDCl$_3$, 300 MHz, 25° C.): δ=7.48 (t, 1H, CHF$_2$, $J_{H\text{-}F}$=52.6 Hz,), 7.04 (t, 1H, CHF$_2$, $J_{H\text{-}F}$=53.8 Hz), 4.38 (q, 2H, CH$_2$, J=7.1 Hz), 4.12 (s, 3H, N—CH$_3$), 1.39 (t, 3H, CH$_3$, J=7.2 Hz) ppm. $^{13}$C NMR (CDCl$_3$, 75 MHz, 25° C.): δ=161.1 (CO), 145.3 (t, C$_{IV}$arom, $J_{C\text{-}F}$=24.9 Hz), 138.2 (t, C$_{IV}$arom, $J_{C\text{-}F}$=24.1 Hz), 112.9 (m, C$_{IV}$arom), 109.1 (t, CHF$_2$, $J_{C\text{-}F}$=237.6 Hz), 107.2 (t, CHF$_2$, $J_{C\text{-}F}$=236.3 Hz), 61.5 (CH$_2$), 39.6 (t, N—CH$_3$, $J_{C\text{-}F}$=3.1 Hz), 1:3.9 (CH$_3$) ppm. $^{19}$F NMR (CDCl$_3$, 282 MHz, 25° C.): δ=−117.00 (CHF$_2$, J$_{F-H}$=53.8 Hz), −117.04 (CHF$_2$, J$_{F-H}$=52.6 Hz) ppm.

Example 13

N-Methyl-3,5-difluoromethyl-4-pyrazolecarboxylic acid

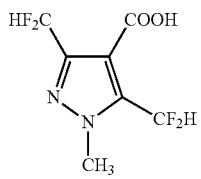

N-Methyl-3,5-difluoromethyl-4-pyrazolecarboxylic acid ethyl ester (0.5 g, 2.0 mmol) in ethanol (3 ml) was admixed gradually with an 8N aqueous sodium hydroxide solution (0.8 ml) and stirred at room temperature for 2 h. The solvent was removed by rotary evaporation; the residue was taken up in water (10 ml) and extracted with diethyl ether (10 ml). Acidification to pH 1 with 6M HCl was followed by extraction with ethyl acetate (3×10 ml). The combined organic phases were dried over sodium sulphate and filtered, and the solvent was removed by rotary evaporation. N-Methyl-3,5-difluoromethyl-4 pyrazolecarboxylic acid (0.44 g, 1.95 mmol, 97%) was isolated as a colourless solid.

$^1$H NMR (CDCl$_3$, 300 MHz, 25° C.): δ=12.16 (brs, 1H, COOH), 7.48 (t, 1H, CHF$_2$, J$_{H-F}$=52.4 Hz), 7.08 (t, 1H, CHF$_2$, J$_{H-F}$=53.6 Hz), 4.16 (s, 3H, N—CH$_3$) ppm. $^{13}$C NMR (CDCl$_3$, 75 MHz, 25° C.): δ=166.9 (CO), 146.4 (t, C$_{IV}$arom, J$_{C-F}$=25.1 Hz), 139.2 (t, C$_{IV}$arom, J$_{C-F}$=24.4 Hz), 111.5 (C$_{IV}$arom), 108.8 (t, CHF$_2$, J$_{C-F}$=238.1 Hz), 106.9 (t, CHF$_2$, J$_{C-F}$=237.0 Hz), 39.9 (t, N—CH$_3$, J$_{C-F}$=3.1 Hz) ppm. $^{19}$F NMR (CDCl$_3$, 282 MHz, 25'C): δ=−117.1 (CHF$_2$, J$_{F-H}$=52.6 Hz), −117.3 (CHF$_2$, J$_{F-H}$=53.7 Hz) ppm.

Example 14

N—H-3,5-Difluoromethyl-4-pyrazolecarboxylic acid ethyl ester

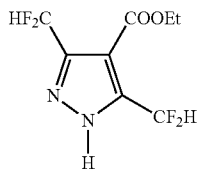

BF$_3$.OEt$_2$ (1.85 ml, 15.0 mmol) was added to a solution of TFEDMA (1.76 ml, 15.0 mmol) in dry dichloromethanes (15 ml) under argon in a Teflon flask. The solution was stirred at room temperature for 15 min, before the dichloromethane was removed under reduced pressure. The residue was then taken up in dry acetonitrile (15 ml). In a second Teflon flask, ethyl 4,4-difluoroacetoacetate (1.55 ml, 15 mmol) was added to a solution of potassium fluorides (2.61 g, 45 mmol) in dry acetonitrile (30 ml) and the mixture was stirred at room temperature for 15 min. To this were added dropwise, at −30° C., the contents of the first flask. The reaction mixture was brought to room temperature in the cold bath and stirred overnight. Hydrazine hydrate (0.1 ml, 22.5 mmol) was then added dropwise at room temperature and the mixture was stirred overnight. The solvent was removed under reduced pressure and the residue was purified by flash chromatography on silica gel with a pentanes/diethyl ether mixture (9:1-7:3), N—H-3,5-Difluoromethyl-4-pyrazolecarboxylic acid ethyl ester (2.02 g, 8.40 mmol, 56%) was isolated as a colourless solid.

$^1$H NMR (CDCl$_3$, 300 MHz, 25° C.): δ=7.15 (t, 2H, CHF$_2$, J$_{H-F}$=53.6 Hz). 4.39 (q, 2H, CH$_2$, J=7.1 Hz), 1.39 (t, 3H, CH$_3$, J=7.1 Hz) ppm. $^{13}$C NMR (CDCl$_3$, 75 MHz, 25° C.): δ=161.1 (CO) 143.8 (t, C$_{IV}$arom, J$_{C-F}$=23.1 Hz), 111.6 (C$_{IV}$arom), 108.2 (t, CHF$_2$, J$_{C-F}$=238.4 Hz), 61.7 (CH$_2$), 1:3.9 (CH$_3$) ppm. $^{19}$F NMR (CDCl$_3$, 282 MHz, 25° C.): δ=−117.3 (CHF$_2$, J$_{F-H}$=53.6 Hz) ppm

The invention claimed is:

1. Process for synthesis of a 3,5-bis(haloalkyl)-pyrazole derivative of formula (I)

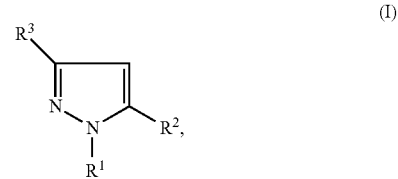

comprising reacting a 3,5-bis(haloalkyl)-pyrazole-4-carboxylic acid derivative of formula (IIa)

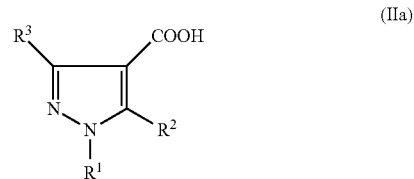

with a copper compound and a base at elevated temperature wherein
R$^1$ is selected from H, C$_{1-12}$-alkyl, C$_{3-8}$-cycloalkyl, C$_{6-18}$-aryl, C$_{7-19}$-arylalkyl or C$_{7-19}$-alkylaryl, CH$_2$CN, CH$_2$CX$_3$, CH$_2$COOH, CH$_2$COO(C$_{1-12}$)-alkyl, and
X is independently of each other F, Cl, Br, I;
R$^2$ and R$^3$ are selected independently of each other from C$_1$-C$_6$-haloalkyl.

2. Process according to claim 1, wherein
R$^1$ is selected from H, C$_{1-12}$-alkyl, CH$_2$CN, CH$_2$COO—(C$_{1-12}$)-alkyl, and
R$^2$ and R$^3$ are selected independently of each other from CF$_3$, CF$_2$H, CF$_2$Cl.

3. Process according to claim 1, wherein
R$^1$ is selected from H, CH$_3$, CH$_2$COO—(C$_{1-12}$)-alkyl, and
R$^2$ and R$^3$ are selected independently of each other from CF$_3$, CF$_2$H, CF$_2$Cl.

4. Process according to claim 1, wherein
R$^1$ is H or CH$_3$.

5. Process according to claim 1, wherein
R$^2$ is CF$_2$H.

6. Process according to claim 1, wherein the base is a mixture of 1,10-phenanthrolin, quinoline and NMP.

7. Process according to claim 1, wherein the base is a mixture of 1,10-phenanthrolin and NMP.

8. Process according to claim 1, wherein the base is a mixture of 1,10-phenanthrolin and quinoline.

9. Process according to claim 1, further comprising adding water.

10. Process according to claim 1, wherein between 0.02 to 0.08 equivalents of water are added for 1 equivalent of pyrazolic acid.

11. Process according to claim 1, wherein reaction temperature is 40° C. to 190° C.

12. Process according to claim 1, wherein reaction temperature is 60° C. to 180° C.

13. Process according to claim 1, wherein reaction temperature is 80° C. to 175° C.

* * * * *